United States Patent
Sommer et al.

(10) Patent No.: US 10,092,744 B2
(45) Date of Patent: Oct. 9, 2018

(54) ACTIVE FIXATION MEDICAL ELECTRICAL LEAD

(71) Applicant: Medtronic, Inc., Minneapolis, MN (US)

(72) Inventors: John L. Sommer, Coon Rapids, MN (US); Linda L. Franke, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 15/229,296

(22) Filed: Aug. 5, 2016

(65) Prior Publication Data

US 2016/0339235 A1     Nov. 24, 2016

Related U.S. Application Data

(63) Continuation of application No. 14/259,904, filed on Apr. 23, 2014.

(51) Int. Cl.
*A61N 1/05* (2006.01)

(52) U.S. Cl.
CPC ...... *A61N 1/0573* (2013.01); *A61N 2001/058* (2013.01); *A61N 2001/0585* (2013.01)

(58) Field of Classification Search
CPC .... A61N 1/057; A61N 1/37205; A61N 1/059; A61N 1/372; A61N 1/375; A61N 2001/058; A61B 2017/22077; A61B 2017/3488; A61B 2018/00273; A61B 5/042; A61B 8/445; A61M 2025/0681; A61M 25/0021; A61M 25/0029
See application file for complete search history.

(56) References Cited

U.S. PATENT DOCUMENTS

| | | | |
|---|---|---|---|
| 5,443,492 A | 8/1995 | Stokes et al. |
| 5,575,814 A | 11/1996 | Giele et al. |
| 6,493,591 B1 | 12/2002 | Stokes |
| 6,556,874 B2 | 8/2003 | Audoglio |
| 7,313,445 B2 | 12/2007 | McVenes et al. |
| 7,529,584 B2 | 5/2009 | Laske et al. |
| 7,532,939 B2 | 5/2009 | Sommer et al. |
| 7,747,333 B2 | 6/2010 | Zarembo et al. |
| 7,860,580 B2 | 12/2010 | Falk et al. |
| 7,890,174 B2 | 2/2011 | Soltis et al. |
| 7,920,927 B2 | 4/2011 | Zarembo et al. |
| 8,551,113 B2 | 10/2013 | Hanse et al. |
| 8,755,909 B2 | 6/2014 | Sommer et al. |

(Continued)

OTHER PUBLICATIONS (PCT/US2015/027030) PCT Notification of Transmittal of the International Search Report and the Written Opinion of the International Searching Authority, dated Jul. 15, 2015, 9 pages.

*Primary Examiner* — Deborah Malamud

(57) ABSTRACT

A medical electrical lead and a method of its use. The lead has an elongated lead body having an outer circumference and provided with an electrode. A push tube is mounted circumferentially around the lead body and the lead body is longitudinally movable with respect thereto. A fixation helix is mounted to the push tube, extending along a generally helical axis around the outer circumference of the lead body. The lead may be employed by advancing the lead to a desired location for the fixation helix and then rotating the push tube to secure the helix to tissue. The lead body may then be moved longitudinally with respect to the push tube to place the electrode in a desirable location.

12 Claims, 5 Drawing Sheets

(56) References Cited

U.S. PATENT DOCUMENTS

2006/0229693 A1 10/2006 Bauer et al.
2007/0250144 A1 10/2007 Falk et al.
2008/0109042 A1 5/2008 Bodner et al.

ACTIVE FIXATION MEDICAL ELECTRICAL LEAD

RELATED APPLICATION

This application is a continuation of U.S. patent application Ser. No. 14/259,904, filed Apr. 23, 2014 entitled "ACTIVE FIXATION MEDICAL ELECTRICAL LEAD", which is herein incorporated by reference in its entirety.

TECHNICAL FIELD

The present invention pertains to medical electrical leads and more particularly to implantable medical electrical leads including active fixation elements.

BACKGROUND

Implantable medical devices, for example cardiac pacemakers and defibrillators, often include elongate medical electrical leads having one or more electrodes to sense electrical activity and deliver therapeutic stimulation. In recent years, with the advent of left ventricular pacing to alleviate heart failure, leads have been advanced into the coronary veins in order to position the electrodes of the leads at left ventricular pacing sites, typically located in proximity to the base of the left ventricle. Although a variety of left ventricular pacing leads, along with methods for implanting such leads, have been developed, there is still a need for a lead including features that facilitate delivery to, and fixation at, sites in the coronary vasculature.

One type of left lead adapted for placement in the coronary vasculature is that disclosed in U.S. Pat. No. 7,860,580, issued to Sommer, et al. and incorporated herein by reference in its entirety. Another type of left lead adapted for placement in the coronary vasculature is that disclosed in U.S. Pat. No. 7,532,939, issued to Sommer, et al. and also incorporated herein by reference in its entirety. An improvement to leads of this type is disclosed in U.S. patent application Ser. No. 13/793,622, filed Mar. 11, 2013 by Sommer, et al. also incorporated herein by reference in its entirety.

Additional designs for a side-helix leads are disclosed in U.S. Pat. No. 5,443,492, issued to Stokes, et al. U.S. Pat. No. 7,529,584, issued to Laske, et al, U.S. Pat. No. 7,313,445, issued to McVenes, et al., U.S. Pat. No. 6,493,591, issued to Stokes, U.S. Pat. No. 6,556,874, issued to Audoglio, all of which are incorporated herein in their entireties.

SUMMARY OF THE INVENTION

The present invention may comprise an improvement to the prior art leads as disclosed in U.S. Pat. No. 7,860,580, cited above. Similarly, the present invention may comprise an improvement to the any of the other prior art leads disclosed in the patents cited above of the same general type, including fixation mechanisms taking the form of a hook or coil extending from the lead body.

In a preferred embodiment, the invention comprises left ventricular (LV) pacing lead having one or more electrodes and having a push tubing overlying the lead body and provided with a fixation mechanism. The fixation mechanism is preferably a fixation helix extending from the push tubing and extending circumferentially around the lead body. The helix may extend distally from a distal end of the push tubing and may be spaced outward from the lead body to define a gap between the two.

In a preferred embodiment, the helix is one which, like that of the above-cited Stokes, et al. '492 patent, extends from the lead body for less than one full turn around the lead body. Preferably, the helix extends from around one half to three quarters of the circumference of the lead body.

The push tubing is preferably rotatable with respect to the lead body and slidable along the length thereof. In use, the lead may be advanced through the vasculature to a desired location, for example by advancing the lead body and push tubing together by means of a guide catheter. When distal end of the guide catheter has reached a desirable location for the fixation mechanism, the lead may be advanced distally out of the guide catheter and the push tubing may be rotated to engage the fixation helix with vascular tissue. The lead body may then be advanced distally through the push tubing to place the electrode or electrodes in a desired location.

After the electrodes are satisfactorily located, the push tubing may then be coupled to the lead body in such a manner as to prevent further relative longitudinal movement, which in turn stabilizes the location of the electrodes relative to the location of the fixation device. In particular, the push tubing and lead body may be stabilized with regard to one another by means of a retention sleeve and/or sutures as described in U.S. Pat. No. 8,551,113 issued to Hanse, et al. and incorporated herein by reference in its entirety. Other retention mechanisms could be substituted, such as those described in U.S. Pat. No. 7,747,333 issued to Zarembo, et al. and U.S. Pat. No. 7,890,174 issued to Soltis, et al., both also incorporated herein by reference in their entireties.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments of the present invention will hereinafter be described in conjunction with the appended drawings, wherein like numerals denote like elements.

DETAILED DESCRIPTION

The following detailed description is exemplary in nature and is not intended to limit the scope, applicability, or configuration of the invention in any way. Rather, the following description provides practical illustrations for implementing exemplary embodiments of the present invention. Constructions, materials, dimensions, and manufacturing processes suitable for making embodiments of the present are known to those of skill in the field of the invention.

Figure 1:
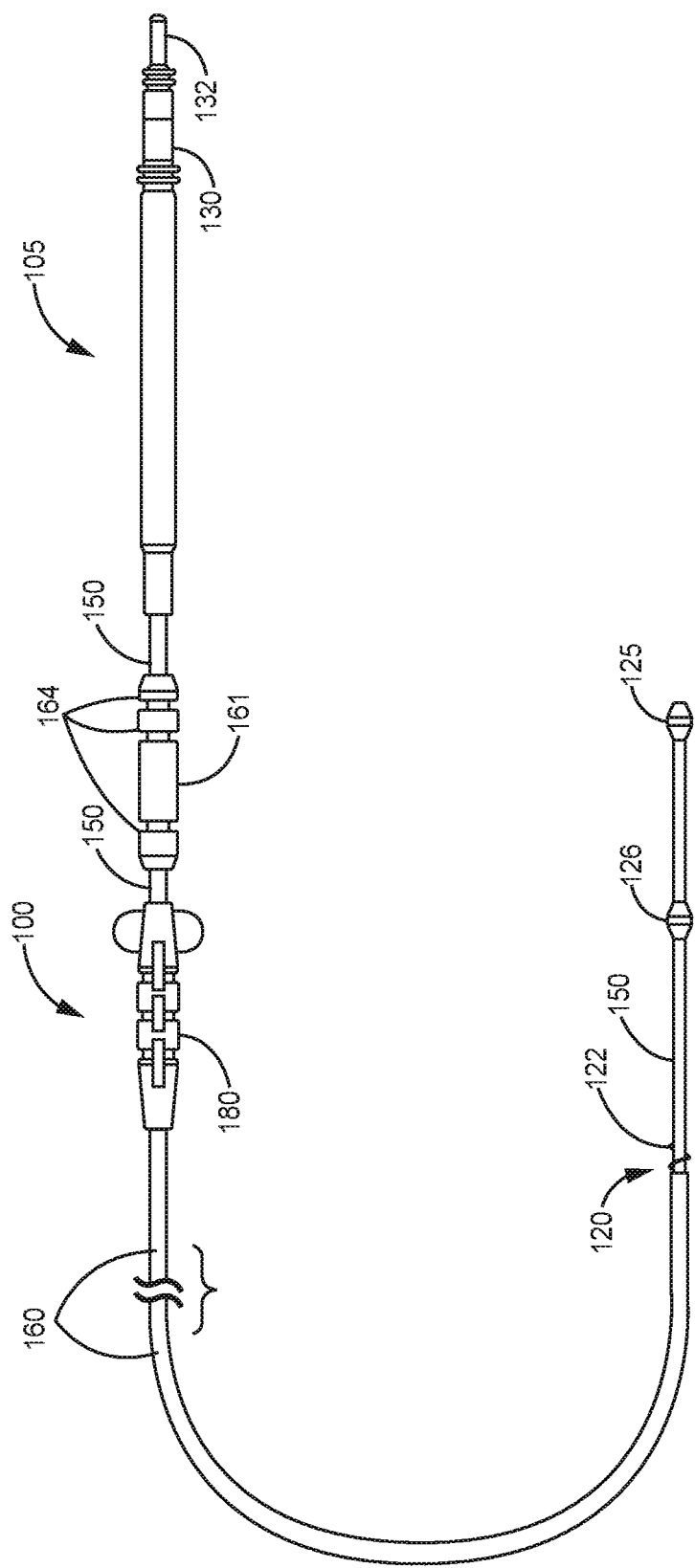
FIG. 1 is a plan view generally illustrating, a lead, according to the invention.

FIG. 1 is a plan view of a lead 100 including a fixation mechanism 120, similar to mechanism 220. Fixation mechanism 120 takes the form of a metal fixation helix mounted to push tube 160, which may be fabricated of an appropriate biocompatible polymer. In the illustrated preferred embodiment, helix 120 has a sharpened free end 122 which extends distally from its attachment point adjacent the distal end of push tube 160 and extends circumferentially around and spaced from lead body 150. In alternative embodiments, the helix 120 might be located proximal to the distal end of 160, extending circumferentially around both the push the 160 and the lead body 150 therein. In still other embodiments, helix 120 may have a free end extending proximally from its attachment point on the push tube 160.

Lead body 150 is sized such that it may be freely moved longitudinally and rotationally within push tube 160, unless otherwise retained in position by means of retention sleeve 161. Sleeve 161 corresponds to that described in the above-cited U.S. Pat. No. 8,551,113 issued to Hanse, et al. According this embodiment of the present invention, retention sleeve 161 includes features adapted to create a frictional interface between fixation mechanism 160 and lead body 150. Retention sleeve 961 may be formed as an independent component, separate from push tube 960 and subsequently fixedly coupled to push tube 160, or may be formed as an integral segment of push tube 160. Sleeve 161 including retention grooves 164 formed on an outer surface thereof. Grooves 164 are adapted to receive a retaining element, which engage grooves to press sleeve 161 against lead body 950, thereby fixedly retaining rube 160 in a prescribed position upon lead body 150 after helix 120 is secured to a desired implant site. According to this embodiment of the present invention, a suture may be tied about each groove or a spring clip fitted about each groove 164 to compress sleeve 161 against lead body 15 so that longitudinal and preferably rotational movement of lead body 150 relative to sleeve 160 is prevented. According to yet another embodiment, one of grooves 164 may accommodates a holding tool to temporarily fix the location if the sleeve 161 relative to lead body 150, as described in the cited Hanse '113 patent. As noted above, other retention mechanisms may be substituted.

Lead body 150 has a proximal portion, to which a connector 105 is coupled, a distal portion along which electrodes 125 and 126 are located. Lead body 150 is formed by an insulative sheath of a biocompatible polymer surrounding internal metallic conductors. The conductors extend from electrodes 125 and 126 to connector 105, coupling the electrodes to contacts 130 and 132 of connector 105 in a conventional fashion. Anchoring sleeve 180 is used in a conventional fashion to stabilize the lead and seal the venous insertion site.

Connector 105 as illustrated takes the firm of an IS-1 bipolar connector, but any appropriate connector mechanism may be substituted. Electrodes 125 and 126 take the form of ring and barrel shaped electrodes, respectively, provided with ring-shaped steroid eluting MCRD's as described in US Patent Publication No. 2006/0229693 by Bauer, et al., incorporated herein by reference in its entirety. Other known electrode designs may of course be substituted.

Figure 2:
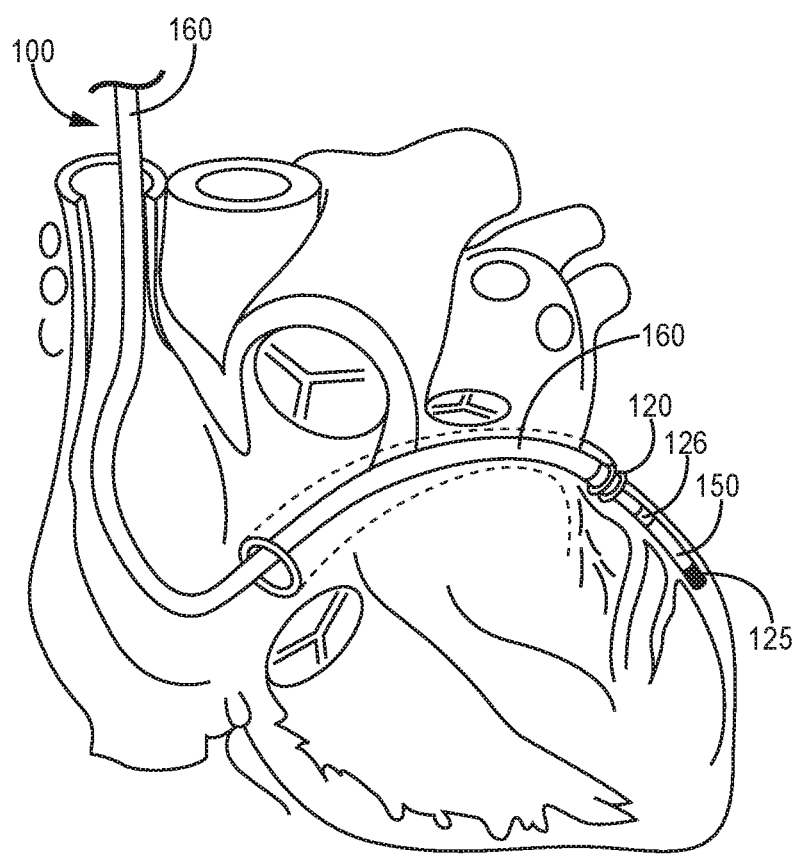
FIG. 2 is an illustration if a human heart and of the lead of FIG. 1 as implanted.
Figure 3:
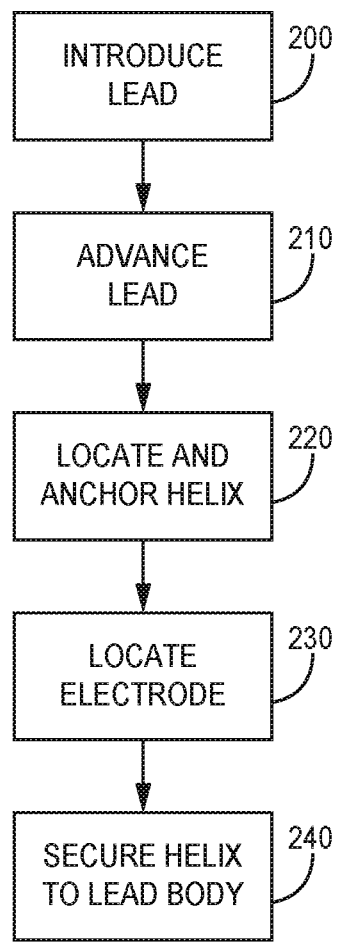
FIG. 3 is a flow chart illustrating the steps of implantation of a lead according to the invention.

FIG. 2 illustrates the location of lead 100 of FIG. 1 as used to provide left ventricular cardiac pacing and or sensing. FIG. 3 is a flow-chart illustrating the steps of lead placement corresponding to the positioning of the lead 100 as illustrated in FIG. 2.

As illustrated, the lead 100 is located in the heart by advancing the lead transvenously into the right atrium and thereafter into the coronary sinus and into a cardiac vein extending therefrom. This may be accomplished by first introducing the lead into the vascular system (step 200, FIG. 3) by any conventional techniques. The lead is then advanced into the coronary venous system (Step 210, FIG. 3). This may be accomplished by passing the lead through a guide catheter or by advancing the lead over a guidewire or by means of a stylet inserted into the lead. Any conventional mechanism for placing the lead into and within the coronary venous system may be employed. If necessary, during advancement of the lead, the push tubing 160 and fixation helix may be rotated opposite the direction of rotation used to attach the fixation helix in order to avoid snagging or entanglement of the helix with vascular or heart tissue.

When helix 120 is located at an appropriate location for fixation, as determined by the physician, the push tubing is rotated to screw the fixation helix into heart tissue (Step 220, FIG. 3). Thereafter, the lead body 150 may be advanced and/or retracted through the push tube 160 until the electrodes 125 and 126 are located in a desirable position (Step 230, FIG. 3). Determination of the position for electrode location may be accomplished by any conventional method, such as pacing threshold texting and/or measurement of R-wave amplitudes. Alternatively or additionally, appropriate electrode locations may also be determined based upon determinations of hemodynamic characteristics of the heart as associated with stimulation of heart tissue at various electrode locations. In some cases, the time order of steps 220 and 230 might be reversed.

Once the electrodes are placed at the desired location, the push tube 160 and fixation helix 120 are coupled to the lead body to prevent subsequent relative longitudinal movement as described above in conjunction with FIG. 1 (Step 240, FIG. 3). Any equipment not intended for long term implant, e.g. guide catheter, stylet, guidewire, etc. can be removed. Repositioning of the electrodes after implant may also be possible.

While FIG. 2 illustrates the electrodes 126 and 125 as located in the great cardiac vein, it should be understood that other locations in the heart's venous system may also be accessed using this lead, including the coronary sinus itself and other cardiac veins. Electrode placement may alternatively be optimized for atrial stimulation and/or sensing. Alternatively, the lead may be useful in other vascular or non-vascular location within the body wherein the distance between a suitable fixation location and a desired electrode location may be variable.

Figure 4:
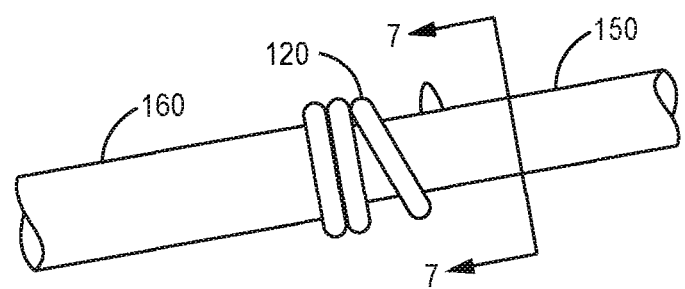
FIG. 4 is a plan view of a portion of a lead as shown generally in FIG. 1, according to a first embodiment.

FIG. 4 shows the fixation helix 120 of FIG. 1 in more detail. In this view, it can be seen that helix 120 takes the form of a multiple turn coil, having one or more close-wound turns encircling the distal portion of push tube 160, with at least a portion of an open-turn extending distally over and spaced from lead body 150. As illustrated, helix 12 has a constant pitch open wound section if approximately ¾ of a turn. Additional open wound turns could be added in alternative embodiments.

FIG. 4 shows an alternative embodiment of the fixation helix. Here, the fixation helix 120A, also takes the form of a multiple turn coil, having one or more close-wound turns encircling the distal portion of push tube 160, with at least a portion of an open-wound turn extending distally over and spaced from lead body 150. However, in this embodiment, an additional plastic component 121 is provided, providing a stop surface generally perpendicular to the helical axis of helix 120A. As described in the above-cited U.S. patent application Ser. No. 13/793,622, filed Mar. 11, 2013 by Sommer, et al., this stop surface prevents pinching and wedging of tissue between the helix and lead body 150.

Figure 5:
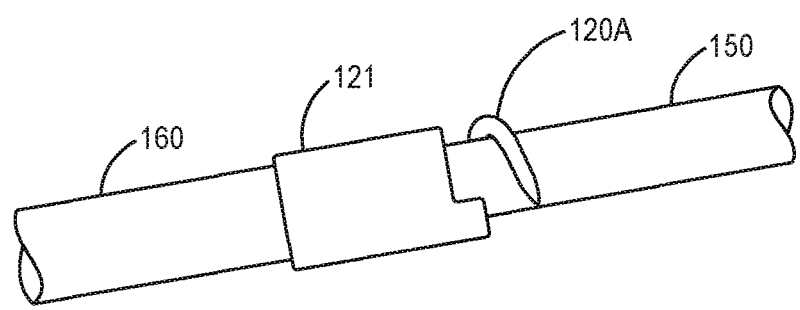
FIG. 5 is a plan view of a portion of a lead as shown in FIG. 1, according to a second embodiment.
Figure 6:
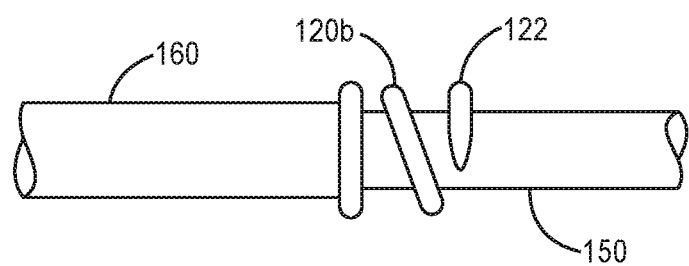
FIG. 6 is a plan view of a portion of a lead as shown in FIG. 1, according to a third embodiment.

FIG. 5 shows an alternative design of a fixation helix 121B wherein the pitch of the open-wound portion of the helix decreases as the distal tip of the helix is reached to a generally zero pitch segment 122, Segment 122 extends essentially perpendicular to the axis of the lead body. Unlike fixation helixes in which the pitch remains constant along their open-wound portions, this embodiment provides a helix that allows for easier tissue entry during rotation of the push tube 160. Additionally, a reduced pitch along the distal tip portion and/or along last winding increases the holding force to the vein wall.

Figure 7:
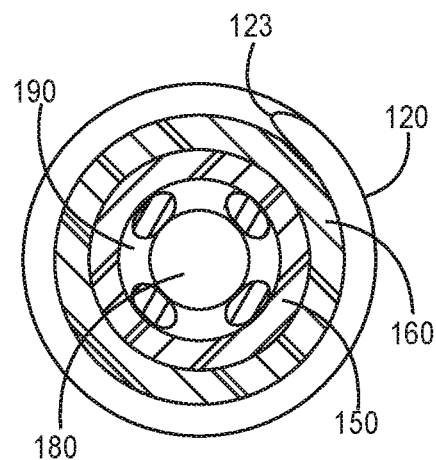
FIG. 7 is a cross sectional view through a lead as generally illustrated in FIG. 1.

FIG. 7 illustrates a cross section through the lead as illustrated in FIG. 4, with numbered components corresponding to identically numbered components in FIGS. 1 and 4. The inside surface 123 of the helix 121 tip is ground to produce a sharpened tip. The inside tip grind allows for a safer passage of the exposed helix at implant and reduces any vein damage that may occur at implant.

Conductors 190 are also illustrated in cross section. In this embodiment, conductors 190 take the form of four filar coil with each filar provided with an insulation coating. In the embodiment of FIG. 1 with two electrodes, typically two filars would be coupled to each electrode. If four electrodes were used, one filar would be coupled to each electrode. If only one electrode is used, all four filars could be coupled to that electrode. Other numbers of filars and other conductor types could be substituted. Use of conductors taking the form of a coil as illustrated provides the benefit of an internal lumen 18 through which a guidewire or stylet may be passed.

In the foregoing detailed description, the invention has been described with reference to specific embodiments. However, it may be appreciated that various modifications and changes can be made without departing from the scope of the invention as set forth in the appended claims.

The invention claimed is:

1. A method of implanting a medical electrical lead:
   wherein the lead comprises an elongated lead body having an outer circumference and provided with an electrode;
   a push tube mounted circumferentially around the lead body and longitudinally movable with respect thereto and having a fixation helix mounted to the push tube extending along a generally helical axis around the outer circumference of the lead body; and
   wherein the method comprises:
   screwing the fixation helix into body tissue;
   thereafter moving the lead longitudinally with respect to the push tube; and
   thereafter securing the lead to prevent further longitudinal movement of the lead body relative to the push tube.

2. A method according to claim 1 wherein the lead further comprises a retention mechanism employable to prevent longitudinal movement of the lead body relative to the push tube and wherein the method further comprises employing the retention mechanism.

3. A method according claim 1 wherein the free end of the fixation helix extends distally from a mounting point on the push tube.

4. A method according to claim 1 wherein the free end of the fixation helix extends distally from the push tube.

5. A method of implanting a medical electrical lead:
   wherein the lead comprises an elongated lead body having an outer circumference and provided with an electrode;
   a push tube mounted circumferentially around the lead body and longitudinally movable with respect thereto and having a fixation helix mounted to the push tube extending along a generally helical axis around the outer circumference of the lead body; and
   wherein the method comprises:
   screwing the fixation helix into body tissue;
   thereafter moving the lead longitudinally with respect to the push tube; and
   thereafter securing the lead to prevent further longitudinal movement of the lead body relative to the push tube; and
   wherein moving the lead longitudinally relative to the push tube comprises moving the lead while the electrode is located distally to the fixation helix.

6. A method according to claim 5 wherein the lead further comprises a retention mechanism employable to prevent longitudinal movement of the lead body relative to the push tube and wherein the method further comprises employing the retention mechanism.

7. A method according claim 5 wherein the free end of the fixation helix extends distally from a mounting point on the push tube.

8. A method according to claim 5 wherein the free end of the fixation helix extends distally from the push tube.

9. A method of implanting a medical electrical lead:
   wherein the lead comprises an elongated lead body having an outer circumference and provided with an electrode;
   a push tube mounted circumferentially around the lead body and longitudinally movable with respect thereto and having a fixation helix mounted to the push tube extending along a generally helical axis around the outer circumference of the lead body; and
   wherein the method comprises:
   screwing the fixation helix into body tissue;
   thereafter moving the lead longitudinally with respect to the push tube; and
   thereafter securing the lead to prevent further longitudinal movement of the lead body relative to the push tube; and
   wherein moving the lead longitudinally relative to the push tube comprises moving the lead distally relative to the fixation helix.

10. A method according to claim 9 wherein the lead further comprises a retention mechanism employable to prevent longitudinal movement of the lead body relative to the push tube and wherein the method further comprises employing the retention mechanism.

11. A method according claim 9 wherein the free end of the fixation helix extends distally from a mounting point on the push tube.

12. A method according to claim 9 wherein the free end of the fixation helix extends distally from the push tube.

* * * * *